US010668474B2

(12) United States Patent
Gottermeier et al.

(10) Patent No.: US 10,668,474 B2
(45) Date of Patent: Jun. 2, 2020

(54) PACKAGING THAT FACILITATES SAMPLE COLLECTION

(71) Applicant: ORTHO-CLINICAL DIAGNOSTICS, INC., Raritan, NJ (US)

(72) Inventors: William Gottermeier, Pittsford, NY (US); Andrew M. Kirsch, Webster, NY (US); Charles E. Declerck, Hilton, NY (US); Aaron M. Swick, Cincinnati, OH (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 178 days.

(21) Appl. No.: 15/744,544

(22) PCT Filed: Jul. 12, 2016

(86) PCT No.: PCT/US2016/041839
§ 371 (c)(1),
(2) Date: Jan. 12, 2018

(87) PCT Pub. No.: WO2017/011429
PCT Pub. Date: Jan. 19, 2017

(65) Prior Publication Data
US 2018/0193847 A1 Jul. 12, 2018

Related U.S. Application Data

(60) Provisional application No. 62/191,550, filed on Jul. 13, 2015.

(51) Int. Cl.
*B01L 9/00* (2006.01)
*A61B 5/15* (2006.01)
(Continued)

(52) U.S. Cl.
CPC ............. *B01L 9/527* (2013.01); *A61B 5/157* (2013.01); *A61B 5/150022* (2013.01);
(Continued)

(58) Field of Classification Search
CPC ........ B01L 9/52; B01L 9/527; B01L 2200/10; B01L 2300/0609; B01K 2200/18;
(Continued)

(56) References Cited

U.S. PATENT DOCUMENTS 5,449,071 A * 9/1995 Levy .................. A61B 10/0096
206/569
7,390,457 B2 * 6/2008 Schembri ............. B01J 19/0046
422/504
(Continued)

FOREIGN PATENT DOCUMENTS

WO WO 2015/086312 A1 6/2015

OTHER PUBLICATIONS

International Search Report and Written Opinion for PCT/US2016/041839; 7 pages.

*Primary Examiner* — Justin N Olamit
(74) *Attorney, Agent, or Firm* — K&L Gates LLP; Louis C. Cullman; Brian J. Novak

(57) ABSTRACT

An article of manufacture composed of tray-like packaging unit characterized by a first section designed to hold a sample analysis slide and a second section designed to hold a sample collection device. Molded into the tray-like packaging unit are a thermoformed well designed to accept a patient's liquid sample from a pipette or syringe, a splash wall formed between the first section and the second section designed to contain the patient's liquid sample in the thermoformed well, and an overflow reservoir designed to hold excess patient sample placed in the thermoformed well. Also molded into the sidewalls of tray-like packaging unit are
(Continued)

Exploded View of Sample Analysis Unit projections designed to allow the sample analysis slide and the sample collection device to be snapped into the packaging unit resulting in a secure configuration for transport.

11 Claims, 5 Drawing Sheets

(51) Int. Cl.
*B01L 3/00* (2006.01)
*A61B 10/00* (2006.01)
*B65D 1/36* (2006.01)
*A61B 5/157* (2006.01)
*A61B 50/30* (2016.01)

(52) U.S. Cl.
CPC .. *A61B 5/150305* (2013.01); *A61B 5/150343* (2013.01); *A61B 10/0045* (2013.01); *A61B 10/0096* (2013.01); *B01L 3/5027* (2013.01); *B65D 1/36* (2013.01); *A61B 5/150358* (2013.01); *A61B 2050/3008* (2016.02); *B01L 2200/04* (2013.01); *B01L 2200/10* (2013.01); *B01L 2200/141* (2013.01); *B01L 2200/18* (2013.01); *B01L 2300/0816* (2013.01)

(58) Field of Classification Search
CPC ........ A61B 5/150305; A61B 5/150755; A61B 10/0096; A61B 50/33; A61B 2050/3008; A61M 5/002; B65D 1/36
See application file for complete search history.

(56) References Cited

U.S. PATENT DOCUMENTS

| | | |
|---|---|---|
| 2004/0214315 A1* | 10/2004 | Saluz .................. B01L 3/50851 435/303.1 |
| 2006/0052810 A1 | 3/2006 | Freeman et al. |
| 2012/0071342 A1* | 3/2012 | Lochhead .......... G01N 21/6452 506/9 |
| 2013/0330713 A1 | 12/2013 | Jakubowicz et al. |
| 2014/0073990 A1* | 3/2014 | Holmes .................. B01L 3/502 600/575 |
| 2014/0272941 A1* | 9/2014 | Gunnerson .......... B01L 3/50273 435/5 |
| 2014/0275866 A1 | 9/2014 | Gunnerson et al. |
| 2015/0320348 A1 | 11/2015 | Ram |

* cited by examiner

Fig. 1 – Complete Sample Analysis Unit as Packaged
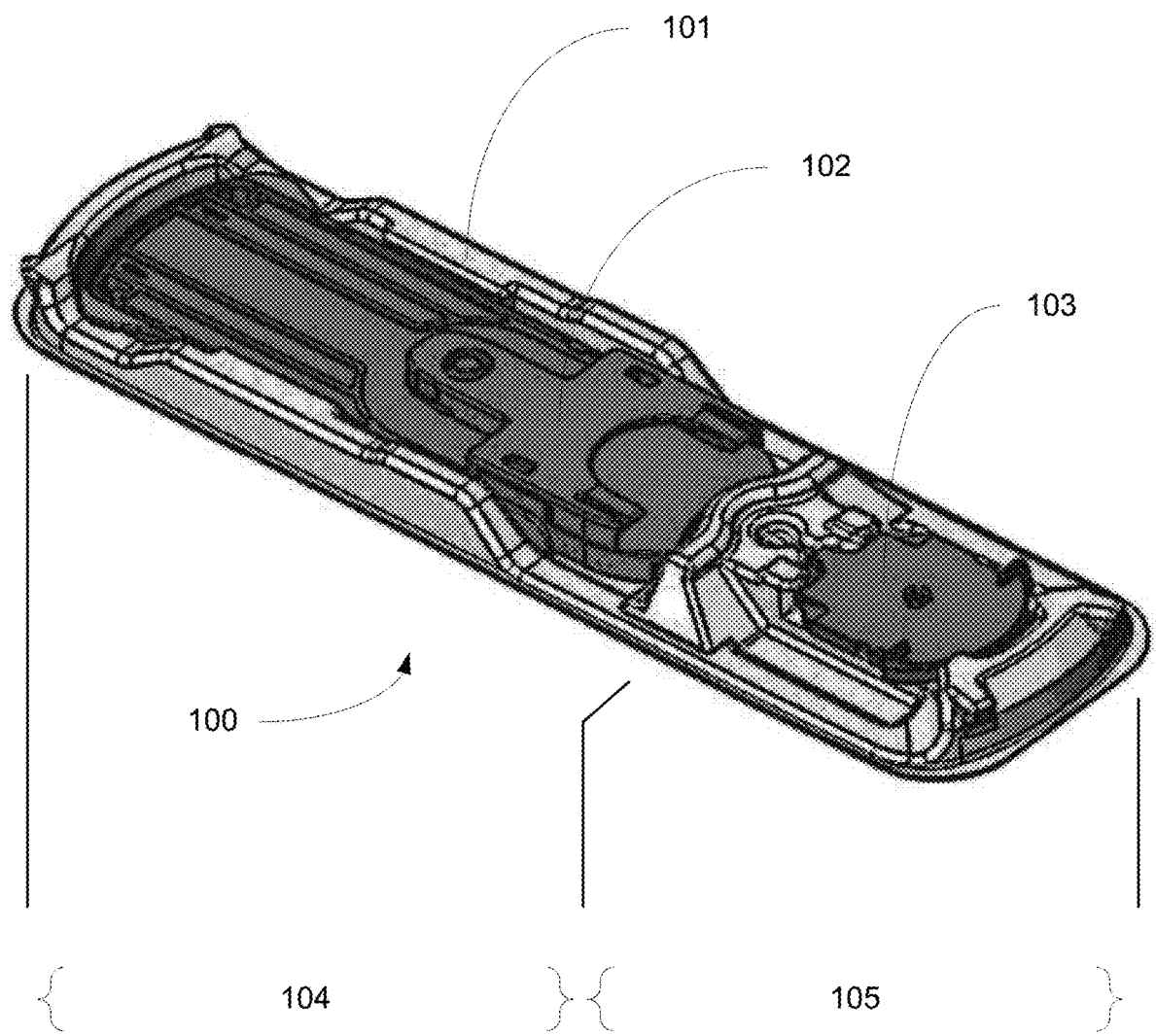

Fig. 2 – Exploded View of Sample Analysis Unit
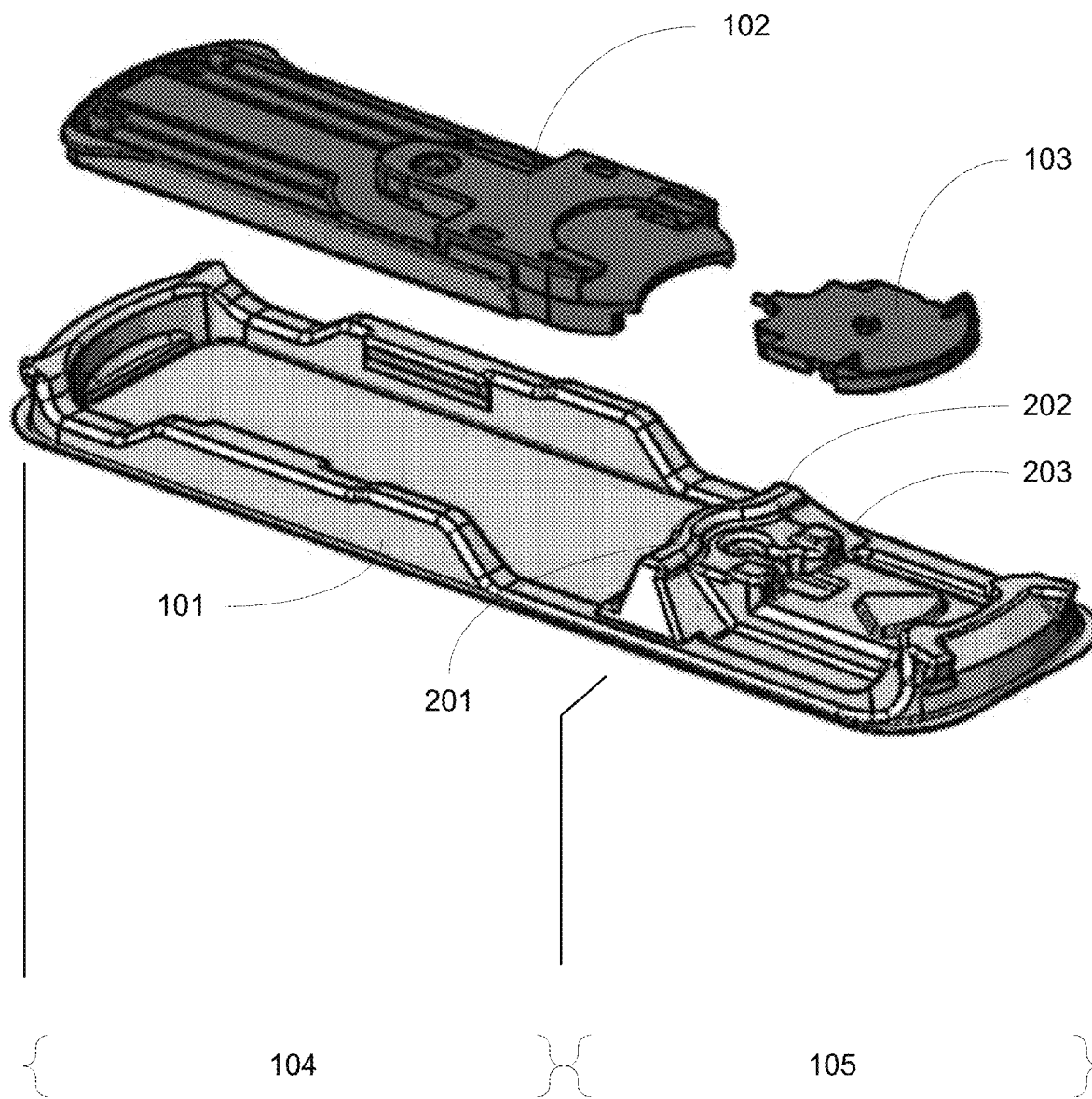

Fig. 3 – Detail of Sample Collection Device Section
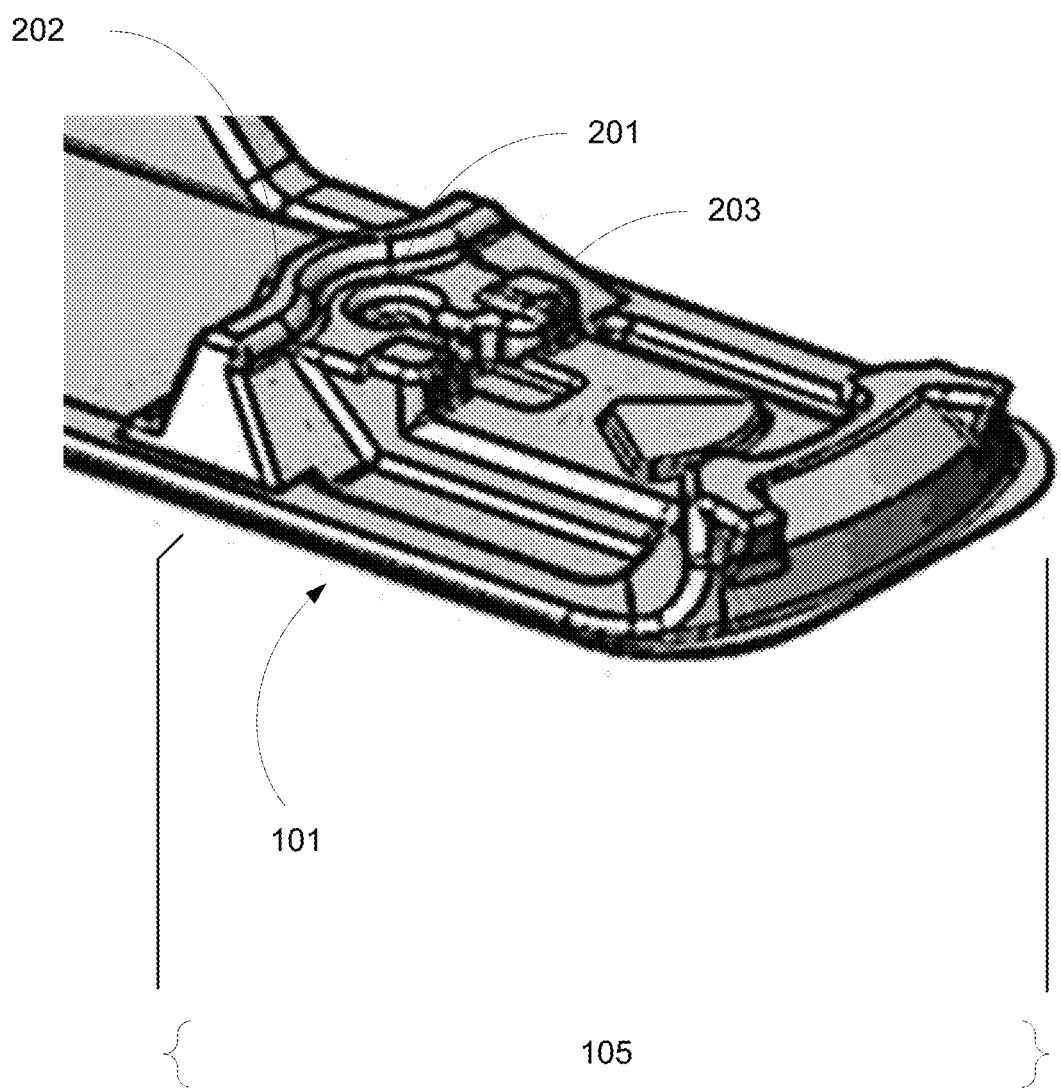

Fig. 4 – Detail of Sample Collection Device Section with Sample Collection Device
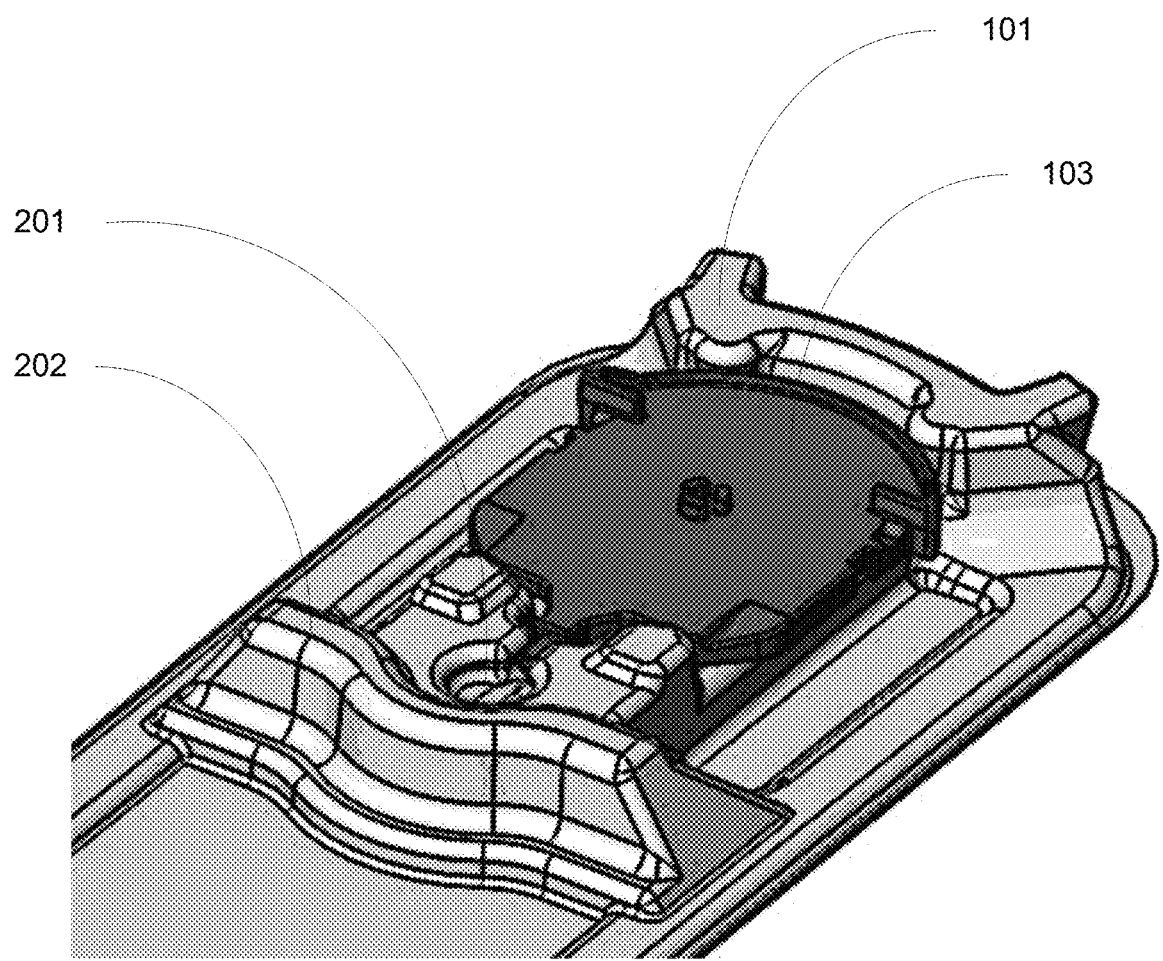

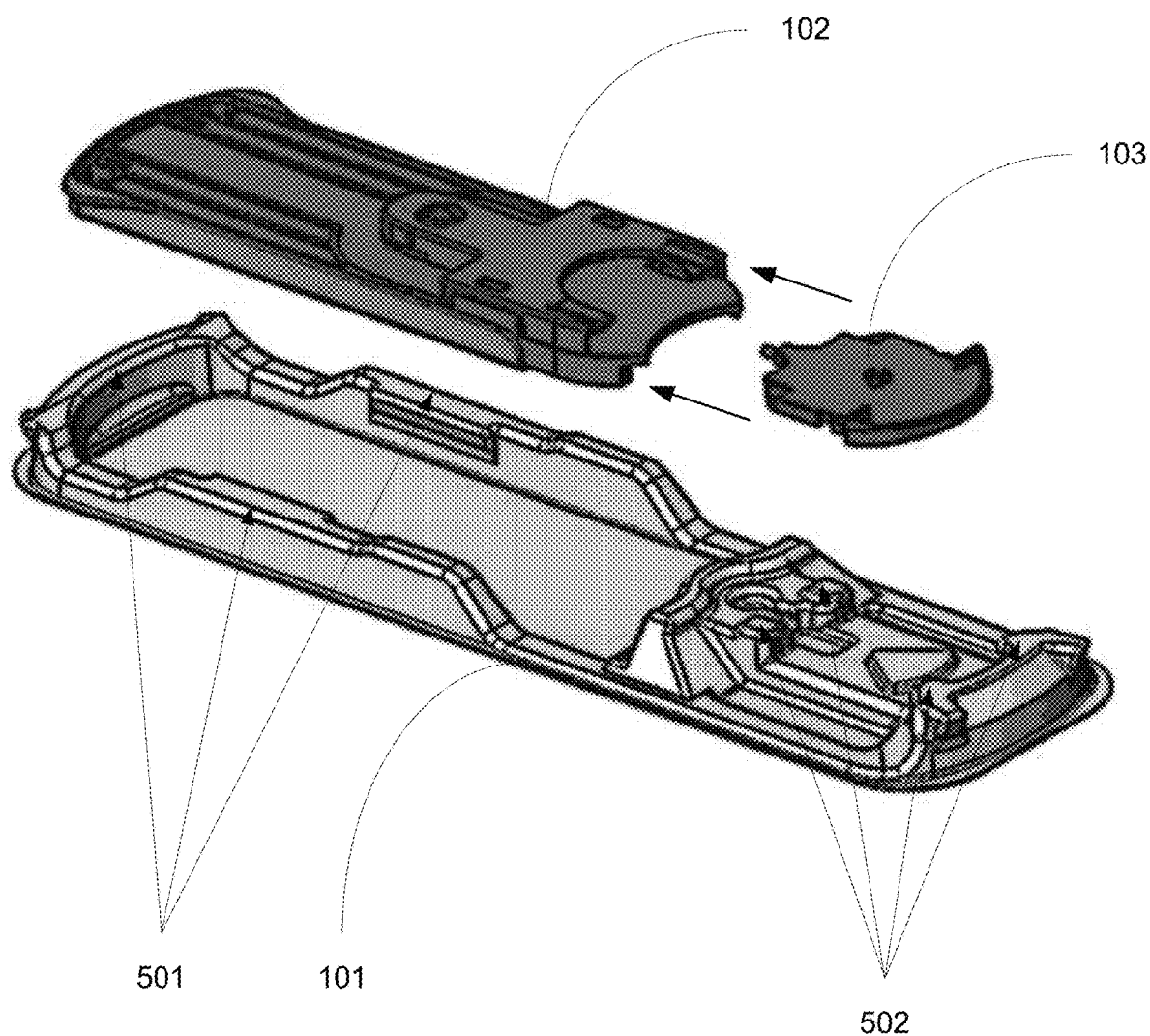
Fig. 5 – Detail of Packaging Unit Showing Snap-In Features

PACKAGING THAT FACILITATES SAMPLE COLLECTION

Cross-Reference to Related Applications

This application is a national stage application under 35 U.S.C. § 371 of International Application No. PCT/US2016/041839, filed Jul. 17, 2016, which claims priority under applicable portions of 35 U.S.C. § 119 of U.S. patent application Ser. No. 62/191,550, filed Jul. 13, 2015, the entire contents of each application being herein incorporated by reference herein.

FIELD OF THE INVENTION

The invention relates generally to a packaging unit used to hold and transport components of a sample analysis unit, which consists of a sample collection device and a sample analysis slide, the sample analysis unit capable of being used as subsystem in in vitro diagnostic analyzers such as a point of care diagnostic device, a benchtop analyzer system, or a mainframe clinical diagnostic analyzer.

BACKGROUND OF THE INVENTION

Over the last several decades significant strides have been made in the development of increasingly automated clinical diagnostic equipment. Initially, the domain of manual laboratory procedures, new diagnostic procedures have been developed for point of care testing requiring little or no equipment, e.g., the Siemens Medical Solutions Diagnostics DCA 2000® HbA1c immunoassay cartridge, for low throughput benchtop analyzers, e.g., Roche Diagnostics" Cobas® c 311 chemistry analyzer, and for high throughput mainframe clinical chemistry analyzers, e.g., Ortho Clinical Diagnostics 5600® analyzer.

Irrespective of the throughput rate of the analyzer, one trend in modern clinical diagnostic analysis is the use of smaller and smaller sample sizes in the diagnostic equipment. Whereas, e.g., in the analysis of blood, once sample sizes in the range of milliliters were required, now in many cases sample sizes in the range of microliters is all that is necessary. The advantage to patients and personnel conducting the sample collection and analysis is significant in that the sample blood draw can often be reduced from a venipuncture (usually collecting about 8.5 mL of blood per tube, up to 3 tubes) to a finger stick (usually collecting about 35 µL of blood); a finger stick also has the potential to minimize the exposure of laboratory personnel to infectious agents and to minimize the potential for hazardous spills. The disadvantage to personnel conducting the sample collection and analysis is the dexterity required to handle and manipulate µL quantities of sample especially when the initial sample is collected via venipuncture.

SUMMARY OF THE INVENTION

One object of the present invention is to provide an article of manufacture, the packaging unit, which aids in the transfer of µLs of a patient liquid sample from a pipette or syringe, holding mLs of a patient's sample, into a sample collection device for further processing.

Another object of the present invention is to enable a method to obtain and conveniently transport just µLs of a patient's sample from a finger stick. Yet another object of the present invention is to provide the packaging unit which supports and securely holds the components of the sample analysis unit during transport to minimize the possibility of mechanical damage.

A further object of the present invention is to minimize the amount of hazardous medical waste generated when using the components of the sample analysis unit.

The foregoing and further objects of the invention are accomplished according to one aspect of the invention that provides a packaging unit, which comprises a first section for holding a sample analysis slide, a second section for holding a sample collection device, a thermoformed well formed in a bottom of the second section adjacent to a splash wall, the splash wall formed between the first section and the second section, and an overflow reservoir formed in the bottom of the second section and in fluidic communication with the thermoformed well.

Still another aspect of the invention provides a method of using a packaging unit to prepare a collected sample for analysis which comprises removing the sample analysis slide from the packaging unit, obtaining a large sample in a pipette or syringe, transferring substantially ½ milliliter of the large sample in a pipette or syringe to the thermoformed well of the packaging unit thereby obtaining a transferred sample, obtaining a collected sample by allowing adequate time for at least part of the transferred sample to be acquired by capillary action into the sample collection device, removing the sample collection device containing the collected sample from the packaging unit, and sliding the sample collection device containing the collected sample into the sample analysis slide thereby forming a combined unit suitable for further analysis.

And yet another aspect of the invention provides a method of using a packaging unit to prepare a collected sample for analysis which comprises removing the sample analysis slide from the packaging unit, removing the sample collection device from the packaging unit, gaining access to a sample, placing the sample collection device in fluidic communication with the sample, obtaining a collected sample by allowing adequate time for at least part of the sample to be acquired by capillary action into the sample collection device, and sliding the sample collection device containing the collected sample into the sample analysis slide thereby forming a combined unit suitable for further analysis.

Further objects, features and advantages of the present invention will be apparent to those skilled in the art from detailed consideration of the preferred embodiments that follow.

BRIEF DESCRIPTION OF THE DRAWINGS

FIG. 1 is a view of the sample analysis unit 100 comprised of a packaging unit 101, a sample analysis slide 102 and a sample collection device 103 as packaged (the impermeable plastic and foil wrap which covers the sample analysis unit 100 during transport is not shown). Also shown are the sample analysis slide section 104 and the sample collection device section 105.

FIG. 2 is an exploded view of FIG. 1 showing the three major components of the sample analysis unit 100, namely, the packaging unit 101, the sample analysis slide 102 and the sample collection device 103. Also shown are the thermoformed well 201, the splash wall 202 and the overflow reservoir 203 that are features molded into the bottom of the tray-like packaging unit 101. Also shown are the sample analysis slide section 104 and the sample collection device section 105.

FIG. 3 is a detailed view of the sample collection device section 105 of the packaging unit 101 that holds the sample collection device 103 (not shown in this figure) showing the features that are molded in, namely, the thermoformed well 201, the splash wall 202 and the overflow reservoir 203.

FIG. 4 is a view of the sample collection device section 105 of the packaging unit 101 with the sample collection device 103 in place. Also shown are the themoformed well 201 and the splash wall 202. The overflow reservoir 203 is beneath the sample collection device 103 tip and cannot be seen.

FIG. 5 is a view of the packaging unit 101 that show assembly features 501 and 502 molded into the sidewalls of the packaging unit 101 that allow both the sample analysis slide 102 and the sample collection device 103 to be snapped into place thereby making those components immobile during transport. Arrows also indicate how the sample collection device 103 once removed from the packaging unit 101 can be inserted and snapped into the sample analysis slide 102 also having been removed from the packaging unit 101.

DETAILED DESCRIPTION OF PREFERRED EMBODIMENTS

While the present invention is described with respect to preferred embodiments as detailed below and shown in the figures, the present invention is limited only by the metes and bounds of the claims that follow.

The tray-like packaging unit 101, an article of manufacture, described herein enables the enhanced handling of a patient's liquid sample taken from a patient undergoing diagnostic testing. Exemplary patient fluids include, but are not limited to, blood, saliva, spinal fluid, semen, vaginal secretions, amniotic fluid, bile, breast milk, mucus, sweat, tears, among others. In particular, the article of manufacture enhances the handling of a patient's fluids contained in pipettes and syringes. No matter as to the liquid sample being acquired from the patient, the various components of the equipment required to perform the blood analysis are conventionally packaged such that the package contents remain sterile, are held at a fixed relative humidity, and are supported in such a manner to avoid mechanical damage when transported. In summary the packaging unit 101 as disclosed improves upon previous packaging and, additionally, aids in the processing of a liquid sample from a patient especially when the sample was collected via venipuncture and also has the potential to minimize the amount of medical waste generated.

The benefits of the article of manufacture, the tray-like packaging unit 101, include (1) providing a stable platform for transport of the sample analysis slide 102 and sample collection device 103 which minimizes the potential for damage, (2) allowing the transfer of a patient's liquid sample from a pipette or syringe via the thermoformed well 201 to a sample collection device 103 for further processing while minimizing both the potential for exposure to infectious agents for laboratory personnel and minimizing the potential for accidental spillage, and (3) if for some reason the patient's sample is to be obtained via finger stick, the sample collection device 103 can be removed from the sample analysis unit 100 and used to acquire the patient's sample directly. In this latter case, the sample analysis slide 102 can be removed from the packaging unit 101 and the packaging unit 101 can be discarded as routine waste, as opposed to medical waste, as it will have not been contaminated by the patient's sample. Another important benefit is that the transfer of a patient's sample from a pipette or syringe to a device such as the sample collection device 103 requires a great deal of manual dexterity raising the possibility of an accidental spill. The use of the packaging unit 101, specifically the thermoformed well 201, significantly reduces this possibility.

For a general understanding of the disclosed article of manufacture, reference is made to the drawings. In the drawings, like reference numerals have been used to designate identical elements. In describing the disclosed article of manufacture, the following term(s) have been used in the description.

The term "tray" or "tray-like" refers to a structure having a substantially rectangular shape with rounded corners, having a substantially flat bottom with upward projections and having sidewalls that project upwards near the edges of the rectangular shape.

The term "packaging unit" refers to an article of manufacture having a tray or tray-like structure constructed of plastic and thermoformed using pressure and heat into the final shape.

The term "sample analysis slide" refers to a diagnostic analytical device using lateral flow technology that inputs a patient's sample from the sample collection device and tests that sample for a particular analyte. Changes in optical density or color allow the response of the sample analysis slide to be read using optical means.

The term "sample collection device" refers to a device that uses capillary action to acquire a patient sample directly, e.g., blood from a finger stick, or indirectly from a pipette or syringe that puts a portion of the sample in the thermoformed well while it is still attached to the packaging unit.

The term "sample analysis unit" refers to the combination of packaging unit, sample analysis slide and sample collection device as initially packaged and shipped.

The term "plastic' refers to one of the commonly use polymers used to produce articles of manufacture using thermoforming which include, but are not limited to acrylonitrile-butadiene-styrene, high-density polyethylene, high impact polystyrene, glycolized polyethylene terephthalate, polycarbonates, polypropylene, and acrylic sheets among others.

FIG. 1 shows the assembled sample analysis unit 100 where the tray-like packaging unit 101 holds the snapped-in sample analysis slide 102 and the sample collection device 103. This sample analysis unit 100 is further encased in a combination plastic and foil wrapper (not shown) during transport to control the humidity of the enclosed air. The sample analysis slide 102 is a lateral flow device capable of receiving a patient's sample from the sample collection device 103 and performing diagnostic tests for one or more target analytes. Typically, these tests are used for medical diagnostics either for home testing, point of care testing, or laboratory use. A widely spread and well known application is the home pregnancy test.

FIG. 2 is an exploded view of FIG. 1 showing the sample analysis slide 102 and the sample collection device 103 removed from the packaging unit 101. Also shown are features molded into the packaging unit 101 including the thermoformed well 201, the splash wall 202 and the overflow reservoir 203. Note that the sample collection device 103 is designed to fit (slide) into the sample analysis slide 102 producing a stable, two-piece unit, thereby enabling the delivery of the patient's sample (contained in the sample collection device 103) into said sample analysis slide 102 as required by the clinical diagnostic analyzer conducting the assay.

FIG. 3 is a detailed view of the sample collection device section 105 of the packaging unit 101. This view shows the thermoformed well 201, the splash wall 202 and the overflow reservoir 203 as thermoformed into the bottom of the tray-like packaging unit 101. The overflow reservoir 203 is hidden under the sample collection device 103 when in the packaged configuration.

FIG. 4 is another detailed view of the sample collection device section 105 of the packaging unit 101, this time showing the sample collection device 103 in the snapped-in and packaged configuration. Also shown are the thermoformed well 201 and the splash wall 202. Note that the tip of sample collection device 103 will be in fluidic communication of any liquid placed in the thermoformed well 201. The tip of the sample collection device 103 supports the end of an open capillary tube of fixed volume such that a known and fixed amount of fluid placed in the thermoformed well 201 will be drawn into the sample collection device 103. The splash wall 202 is present to prevent the inadvertent distribution of patient sample into or on the sample analysis slide 102 side of the splash wall 202. The overflow reservoir 203 (hidden under the sample collection device 103) is also in fluidic communication with any sample placed in the thermoformed well 201 and serves to take up excess patient sample that might be placed in the thermoformed well 201.

FIG. 5 is a view of the components of the sample analysis unit 100 showing the three major components, i.e., the packaging unit 101, the sample analysis slide 102 and the sample collection device 103. Also noted are the snap-in features 501 and 502 molded into the sidewalls of the tray-like packaging unit 101 that allow the sample analysis slide 102 and the sample collection device 103, respectively, to be snapped into place and securely held immobile during transport. The arrows in this view also indicates how the sample collection device 103, after obtaining a patient's sample, may be slid into the sample analysis slide 102 which also has features (not shown) which snap the sample collection device 103 into the sample analysis slide 102 creating a two-piece unit which is input into a clinical diagnostic analyzer for subsequent processing and assay readout.

In one preferred embodiment, the sample collection section 105 of the packaging unit 101 can be separated from the sample analysis slide section by a perforation, (not shown). This feature the sample analysis slide 102 and the collection device 103 to be separated with removing them from the packaging unit 101. This has the advantage of reducing medical waste because only the sample collection section 105 is contaminated by a patient sample.

EXAMPLE 1

Fingerstick Sample Source

In this example, a patient's sample of blood is to be obtained via a finger stick where a sharp instrument or lance is used to effect a small laceration in the tip of a finger. The personnel collecting the sample will have beforehand removed the plastic and foil wrapper from the sample analysis unit 100 and, subsequently, removed both the sample analysis slide 102 and sample collection device 103 from the packaging unit 101. After the laceration has been effected, the patient's finger is often squeezed to produce a drop of blood on the fingertip. The tip of the sample collection device 103 is then applied to the drop of blood and the sample collection device 103 then takes in, by capillary action, a fixed amount of patient sample. The sample collection device 103 is then inserted into the right end of the sample analysis slide 102 and is snapped into place. This two-piece unit of Slide and Chip prevents leakage of the patient sample, thereby reducing the possibility of a hazardous medical waste spill, and allows transport on the combined unit to a clinical diagnostic analyzer processor-reader for further processing. Upon insertion of the combined unit into the clinical diagnostic analyzer processor-reader the processing protocol uses air pressure to move the patient sample from the sample collection device 103 into the sample analysis slide 102. Further processing in the clinical diagnostic analyzer processor-reader produces a change in optical density or color which upon being optically read produces an assay result. A general discussion of lateral flow slide devices in mainframe clinical diagnostic analysis is disclosed in the co-pending U.S. patent application publication 20130330713A1 entitled "Lateral Flow Assay Devices for Use in Clinical Diagnostic Apparatus and Configuration of Clinical Diagnostic Apparatus for Same" by Jakubowicz, Bower, Dambra, Ding, Robinson, Ryan and Tomasso which is hereby incorporated in its entirety by reference. In this example, the packaging unit 101 and plastic and foil wrapper can be discarded as regular waste while the combined unit must be discarded as hazardous medical waste.

EXAMPLE 2

Pipette or Syringe Sample Source

In this example, a patient sample is already available having been obtained via a venipuncture where the sample now resides in a pipette or syringe. Unlike in Example 1 above, the person collecting the sample will have beforehand removed the plastic and foil wrapper from the sample analysis unit 100 and, but subsequently, only removed the sample analysis slide 102 from the packaging unit 101. The sample collection device 103 remains in the packaging unit 101.

Assuming that the pipette or syringe contains upward of 10 mL of patient sample, forming a drop of about 35 μL on the tip of the pipette or syringe takes significant manual dexterity with a corresponding increase in the possibility of a hazardous medical waste spill. To eliminate this awkward procedure with the sample collection device 103 still embedded in the packaging unit 101, it is a relative easy maneuver to dispense a somewhat larger quantity of patient sample, say on the order of 0.1 to 0.2 mL, into the thermoformed well 201 of the packaging unit 101. As the tip of the sample collection device 103 is in fluid communication with any liquid put into the thermoformed well 201, a fixed quantity of the patient sample is drawn into the sample collection device 103 by capillary action. Excess patient sample placed in the thermoformed well 201 is taken up by the overflow reservoir 203. The sample collection device 103 now containing the patient sample is removed from the packaging unit 101 then inserted into the sample analysis slide 102 and snapped into place. Processing now continues as in Example 1 above except that the packaging unit 101 must be discarded as medical waste.

ADDITIONAL EMBODIMENTS

1. A packaging unit, which comprises: a first section for holding a sample analysis slide, a second section for holding a sample collection device, a thermoformed well formed in a bottom of the second section adjacent to a splash wall, said splash wall formed between said first section and said second section, and an overflow reservoir formed in said bottom of the second section and in fluid communication with said thermoformed well.

2. A packaging unit as disclosed in embodiment 1, further comprising: at least one snap in projection formed in a side wall of the first section designed to hold said sample analysis slide securely in place, and at least on snap in projection formed in a side wall of the second section designed to hold said sample collection device securely in place.

3. A packaging unit as disclosed in embodiment 2, where the packaging unit is constructed of a plastic selected from one of the following: acrylonitrile-butadiene-styrene, high-density polyethylene, high-impact polystyrene, polycarbonates, polypropylene, and acrylic sheets.

4. A packaging unit as disclosed in embodiment 1, further comprising a perforation for separating the first and second section.

5. A method of using a packaging unit as disclosed in embodiment 1 to prepare a collected sample for analysis which comprises: removing the sample analysis slide from the packaging unit, obtaining a sample in a pipette or syringe, transferring at least a portion of said sample in a pipette or syringe to the thermoformed well of said packaging unit thereby obtaining a transferred sample, obtaining a collected sample by allowing adequate time for at least part of said transferred sample to be acquired by capillary action into the sample collection device, removing the sample collection device containing the collected sample from the packaging unit, and sliding the sample collection device containing the collected sample into the sample analysis slide thereby forming a combined unit suitable for further analysis.

6. A method as disclosed in embodiment 5, wherein the step of removing the sample analysis slide from the packaging unit is any time before the step of sliding the sample collection device containing the collected sample into the sample analysis slide thereby forming a combined unit suitable for further analysis.

7. A method as disclosed in embodiment 5, wherein about ½ milliliter of the sample is transferred from the pipette or syringe into the thermoformed well.

8. A method as disclosed in embodiment 5, further comprising a perforation for separating the first and second section and wherein said first and second sections are separated at the perforations before the step of transferring at least a portion of said sample in a pipette or syringe to the thermoformed well.

9. A method of using a packaging unit as disclosed in embodiment 1 to prepare a collected sample for analysis which comprises: removing the sample analysis slide from the packaging unit, removing the sample collection device from the packaging unit, gaining access to a sample, placing the sample collection device in fluidic communication with the sample, obtaining a collected sample by allowing adequate time for at least part of said sample to be acquired by capillary action into the sample collection device, and sliding the sample collection device containing the collected sample into the sample analysis slide thereby forming a combined unit suitable for further analysis.

10. A method as disclosed in embodiment 8, wherein the step of removing the sample analysis slide from the packaging unit is any time before the step of sliding the sample collection device containing the collected sample into the sample analysis slide thereby forming a combined unit suitable for further analysis.

11. A method as disclosed in embodiment 8, wherein the sample is a finger stick of blood.

It will be apparent to those skilled in the art that various modifications and variations can be made to the article of manufacture disclosed herein. Thus, it is intended that the present invention cover such modifications and variations, provided they come within the scope of the appended claims and their equivalents.

The disclosure of all publications cited above is expressly incorporated herein by reference in their entireties to the same extent as if each were incorporated by reference individually.

We claim:

1. A packaging unit, which comprises:
   a first section including a removable sample analysis slide;
   a second section including a removable sample collection device, wherein the removable sample analysis slide includes a location into which the removable sample collection device can be inserted;
   a thermoformed well formed in a bottom of the second section adjacent to a splash wall, wherein said splash wall is located between the first section and the second section; and
   an overflow reservoir located in the bottom of the second section and in fluidic communication with the thermoformed well.

2. The packaging unit as recited in claim 1, further comprising:
   at least one snap-in projection formed in a side wall of the first section designed to hold the removable sample analysis slide securely in place, and
   at least one snap-in projection formed in a side wall of the second section designed to hold the removable sample collection device securely in place.

3. The packaging unit as recited in claim 2, in which the packaging unit is constructed from a plastic selected from one or more of the following:
   acrylonitrile-butadiene-styrene, high-density polyethylene, high impact polystyrene, glycolized polyethylene terephthalate, polycarbonates, polypropylene, and acrylic sheets.

4. The packaging unit as recited in claim 1, further comprising a perforation for separating the first and second sections.

5. A method of using a packaging unit as recited in claim 1, to prepare a collected sample for analysis which comprises:
   removing the removable sample analysis slide from the packaging unit;
   obtaining a sample in a pipette or syringe;
   transferring at least a portion of the sample in a pipette or syringe to the thermoformed well of the packaging unit, thereby obtaining a transferred sample;
   obtaining a collected sample by allowing adequate time for at least part of the transferred sample to be acquired by capillary action into the removable sample collection device;
   removing the removable sample collection device containing the collected sample from the packaging unit; and
   sliding the removable sample collection device containing the collected sample into the removable sample analysis slide, thereby forming a combined unit suitable for further analysis.

6. The method as claimed in claim 5, wherein the step of removing the removable sample analysis slide from the packaging unit is performed any time before the step of sliding the removable sample collection device containing the collected sample into the removable sample analysis slide thereby forming a combined unit suitable for further analysis.

7. The method as claimed in claim 5, wherein about ½ milliliter of sample is transferred from the pipette or syringe into the thermoformed well.

8. The method as claimed in claim 5, further comprising a perforation for separating the first and section and wherein the first and second sections are separated at the perforation before the step of transferring at least a portion of the sample in a pipette or syringe to the thermoformed well.

9. The method as claimed in claim 8, wherein the step of removing the removable sample analysis slide from the packaging unit is performed any time before the step of sliding the removable sample collection device containing the collected sample into the removable sample analysis slide, thereby forming a combined unit suitable for further analysis.

10. The method as claimed in claim 8, wherein the sample is a finger stick of blood.

11. A method of using a packaging unit as recited in claim 1, to prepare a collected sample for analysis which comprises:
  removing the removable sample analysis slide from the packaging unit;
  removing the removable sample collection device from the packaging unit;
  gaining access to a sample;
  placing the removable sample collection device in fluidic communication with the sample;
  obtaining a collected sample by allowing adequate time for at least part of the sample to be acquired by capillary action into the removable sample collection device; and
  sliding the removable sample collection device containing the collected sample into the removable sample analysis slide, thereby forming a combined unit suitable for further analysis.

\* \* \* \* \*